United States Patent [19]

Brion et al.

[11] Patent Number: 4,975,454

[45] Date of Patent: Dec. 4, 1990

[54] TRIENE COMPOUNDS HAVING A CHROMENE STRUCTURE

[75] Inventors: Jean-Daniel Brion, Saint-Leu La Foret; Guillaume Le Baut, Saint-Sebastien sur Loire; Patrick Ducrey, Rueil Malmaison; Sylvie Piessard-Robert, Nantes; Claude Cudennec, La Celle Saint-Cloud; Geneviève Seurre, Paris, all of France

[73] Assignee: Adir et Compagnie, Neuilly-sur-Seine, France

[21] Appl. No.: 336,225

[22] Filed: Apr. 11, 1989

[30] Foreign Application Priority Data

Apr. 13, 1988 [FR] France .................. 88 04871

[51] Int. Cl.$^5$ .................. A61K 31/35; C07D 311/58
[52] U.S. Cl. .................. 514/456; 549/407
[58] Field of Search .................. 549/407; 514/456

[56] References Cited

U.S. PATENT DOCUMENTS 4,833,254  5/1989  Berlin et al. .................. 548/454

OTHER PUBLICATIONS

Suffness et al., J. Natural Products, 45, pp. 1–14 (1982).
The Lancet, Apr. 16, 1983, pp. 860 through 863, "Nutrition: The Changing Scene".

"Nomenclature of Organic Chemistry", 1979 Edition, pp. 476 through 477 plus cover sheet.

*Primary Examiner*—Nicky Chan
*Attorney, Agent, or Firm*—Gordon W. Hueschen

[57] ABSTRACT

Compounds of general formula (I):

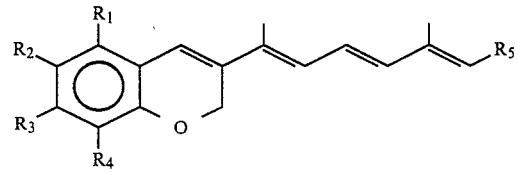

in which:

$R_1$, $R_2$, $R_3$ and $R_4$, which may be identical or different, denote a hydrogen atom, a halogen atom or a lower alkyl, lower alkenyl, lower alkyloxy or lower alkenyloxy group, optionally substituted with one or more halogen atoms, $R_5$ denotes a carboxyl, (lower alkyloxy)carbonyl, (lower alkenyloxy)carbonyl or (lower alkynyloxy)-carbonyl, their isomers, stereoisomers and diastereoisomers, and also their addition salts with a pharmaceutically acceptable base.

Medicinal products.

8 Claims, No Drawings

TRIENE COMPOUNDS HAVING A CHROMENE STRUCTURE

The present invention relates to new compounds endowed with anticancer properties belonging to the retinoid family, to a process for preparing them and to pharmaceutical compositions containing them.

Many substances of the retinoid family which are renowned for their anticancer properties are known. U.S. Pat. Nos. 4,054,589, 4,106,681, 4,137,246, 4,165,103, 4,169,100, 4,171,318, 4,224,244, BE No. 861,982, FR No. 2,556,348 and EP No. 111,124 describe compounds of the retinoid family in which the tetraene chain is attached to a monocyclic structure based on cyclohexene or benzene.

More especially, U.S. Pat. No. 4,105,681 describes etretinate, used in therapy, and whose anticancer properties are known at the present time.

U.S. Pat. No. 4,321,209 as well as Priority Documents DT No. 2,542,600 and DT No. 3,542,601 describe compounds in which the triene chain is attached to an aromatic monocyclic structure.

The needs of therapy demand the constant development of new anticancer agents, with the dual objective of obtaining molecules which are more active but, at the same time, less toxic.

The derivatives of the present invention possess a novel structure consisting of a triene chain attached to a bicyclic structure of the chromene type, which is to be found in many natural substances, the structure optionally being substituted on the aromatic ring. The novelty of the structure of the compounds of the present invention makes it possible to obtain especially advantageous pharmacological properties, since the latter prove, in the tests studied, to be superior to that of etretinate. In addition, their toxicity is especially low, since it was found that these compounds caused no excess-vitamin A toxicity, in contrast to etretinate.

More especially, the subject of the present invention is products of general formula (I):

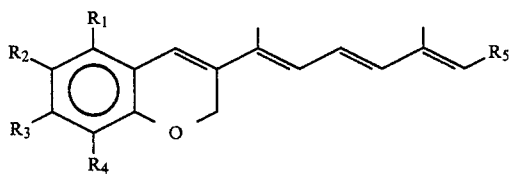

in which:
$R_1$, $R_2$, $R_3$ and $R_4$, which may be identical or different, denote a hydrogen atom, a halogen atom or a lower alkyl, lower alkenyl, lower alkyloxy or lower alkenyloxy group, optionally substituted with one or more halogen atoms, $R_5$ denotes a carboxyl, (lower alkyloxy)carbonyl, (lower alkenyloxy)carbonyl or (lower alkynyloxy)-carbonyl, their isomers, stereoisomers and diastereoisomers, and also their addition salts with a pharmaceutically acceptable base.

Among bases capable of salifying the compounds of formula (I) in which $R_5$ denotes a carboxyl group, there may be mentioned, by way of example, sodium hydroxide, potassium hydroxide, calcium hydroxide or aluminum hydroxide, alkali metal or alkaline-earth metal carbonates, or organic bases such as triethylamine, benzylamine, diethanolamine, tert-butylamine, dicyclohexylamine, arginine, and the like.

Lower alkyl, lower alkenyl, lower alkyloxy, lower alkenyloxy and lower alkynyloxy radicals are understood to mean linear or branched groups comprising between 1 and 6 carbon atoms.

The present invention also encompasses a process for preparing the compounds of formula (I), wherein a compound of formula (II):

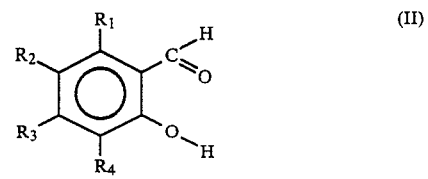

in which $R_1$, $R_2$, $R_3$ and $R_4$ have the same meaning as in the formula (I),
is condensed by heating under reflux of the solvent with 3-oxo-1-butene of the formula (III):

in the presence of an alkaline agent preferably chosen from alkali metal and alkaline-earth metal carbonates, or organic bases such as, for example, triethylamine or pyridine, or a mixture consisting of an alkali metal carbonate or alkaline-earth metal carbonate and an organic base, in a polar solvent preferably chosen from ketonic solvents such as 2-butanone or amidic solvents such as dimethylformamide, to lead, after cooling and, where appropriate, evaporation of the reaction medium, taking up with water to which an alkaline agent such as sodium hydroxide has been added where appropriate, extraction with a suitable organic solvent such as diethyl ether, chloroform or methylene chloride, washing of the organic phase, evaporation of the solvent and purification of the residue by crystallization or distillation or chromatography on a silica or alumina column, to a compound of formula (IV):

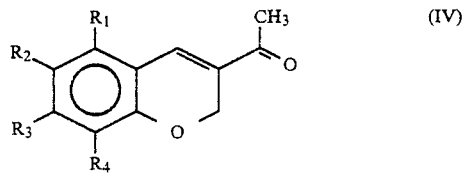

in which $R_1$, $R_2$, $R_3$ and $R_4$ have the same meaning as in formula (I), which compound is subjected
  * either to catalytic hydrogenation, after dissolution in a suitable organic solvent preferably chosen from lower aliphatic alcohols, preferably in the presence of an alkaline agent such as sodium hydroxide, the hydrogenation preferably being carried out with an alkali metal mixed hydride such as sodium borohydride, to lead, after extraction with a suitable organic solvent such as diethyl ether, dichloromethane or chloroform, preceded where appropriate by evaporation of the reaction medium, washing, then evaporation of the organic phase and purification, to a compound of formula (V):

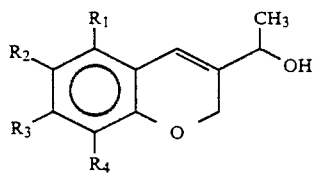

(V)

in which $R_1$, $R_2$, $R_3$ and $R_4$ have the same meaning as above,
which compound is subjected to the action of a triphenylphosphonium salt in a solvent preferably chosen from lower aliphatic alcohols, at room temperature and with stirring, to lead, after evaporation of the solvent and purification by chromatography on silica gel or by crystallization in a solvent or a mixture of suitable solvents,
to a compound of formula (VI):

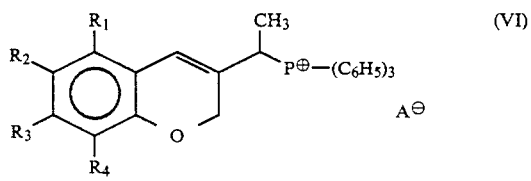

(VI)

in which $A^-$ denotes the anion of a hydracid and $R_1$, $R_2$, $R_3$ and $R_4$ have the same meaning as above, which is subjected, in a suitable solvent, preferably under an inert atmosphere and in the presence of n-butyllithium in hexane, to the action of a stereochemically blocked dienic aldehyde in the form of a tricarbonyliron complex of formula (VII) according to the reaction described by WITTIG (Ber 1954, 87, 1318 and Ber 1955, 88, 1654):

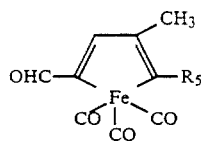

(VII)

in which $R_5$ has the same meaning as in the formula (I), at a temperature preferably of between $-5°$ C. and $-30°$ C., and preferably of between $-15°$ C. and $-20°$ C., to lead, after extraction with a suitable solvent, washing and evaporation of the organic phase, to an intermediate complex which, after purification by chromatography, is subjected, under reflux of the organic solvent chosen for this stage, to the action of trimethylamines with N-oxide, to lead, after cooling, extraction with a suitable organic solvent, washing and evaporation of the organic phase and column chromatography, to a compound of formula (I),

* or to the action of ethyl bromoacetate in the presence of zinc, followed by a hydrolysis of the reaction medium at the required moment and extraction with a suitable organic solvent preferably chosen from ethyl acetate, methylene chloride, chloroform and diethyl ether, and then to the action of phosphorus oxychloride in a suitable organic solvent, evaporation of the reaction medium and a further extraction with a solvent preferably chosen from ethyl acetate, methylene chloride, chloroform and diethyl ether, to lead, where appropriate after chromatography on silica gel, to a compound of formula (VIII)

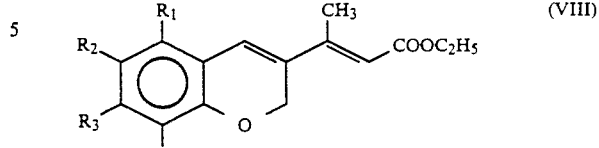

(VIII)

in which $R_1$, $R_2$, $R_3$, and $R_4$ have the same meaning as in the formula (I),
which is subjected at a low temperature preferably of between $-50°$ and $0°$ C., and preferably between $-25°$ and $5°$ C., in a solvent preferably chosen from diethyl ether, diisopropyl ether and tetrahydrofuran, to the action of lithium aluminum hydride, to lead to a compound of formula (IX):

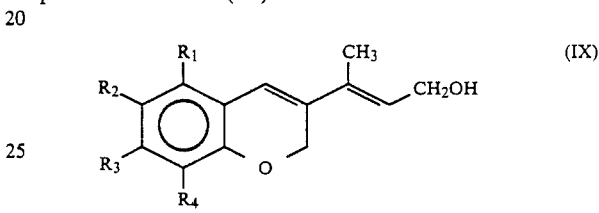

(IX)

in which $R_1$, $R_2$, $R_3$ and $R_4$ have the same meaning as in the formula (I),
which is subjected to oxidation with manganese dioxide to lead, after chromatography on silica gel and crystallization where appropriate, to a derivative of formula (X):

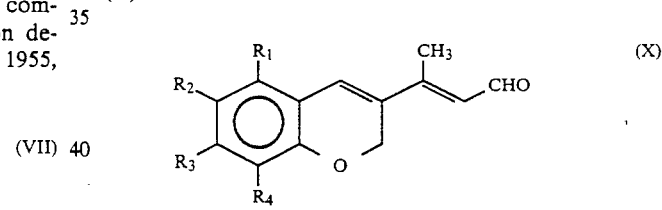

(X)

in which $R_1$, $R_2$, $R_3$ and $R_4$ have the same meaning as in the formula (I), which is subjected to the action of a compound of formula (XI) according to the WADSWORTH-EMMONS reaction (J. Am. Chem. Soc. 1961, 83, 1733)

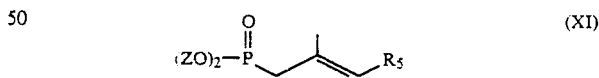

(XI)

in which $R_5$ has the same meaning as in the formula (I) and Z is a lower alkyl group, at room temperature, to lead, after extraction with a suitable organic solvent, evaporation and purification by chromatography on a silica column, to a compound of formula (I),
which can, if so desired,
either, when $R_5$ denotes a carboxyl group, be salified with a pharmaceutically acceptable base,
or be separated into its stereoisomers by a technique of crystallization or chromatography and then, if so desired, when $R_5$ denotes a carboxyl group, be salified with a pharmaceutically acceptable base.

The compounds of formula (I) possess very advantageous pharmacological properties. They strongly inhibit the growth of L 1210 line in mice, have an activity on the differentiation of HL 60 line cells and, an especially advantageous factor for their use in therapy, do not appear to cause excess-vitamin A toxicity, which is induced by etretinate and the symptoms of which are rapid weight loss, alopecia and bone weakening.

The compounds according to the present invention hence find a use in therapy as antitumor agents, for the treatment or prophylaxis of benign or malignant neoplasms, as well as in the traditional indications for retinoids, such as skin disorders (acne, psoriasis), as well as degenerative disorders and/or inflammation of the mucosae.

The subject of the present invention is also the pharmaceutical compositions containing the products of the formula (I), or one of their addition salts with a pharmaceutically acceptable base when $R_5$ denotes a carboxyl group, alone or in combination with one or more pharmaceutically acceptable, non-toxic, inert vehicles or excipients.

Among the pharmaceutical compositions according to the invention, there may be mentioned, more especially, those which are suitable for oral, parenteral, nasal, rectal, perlingual, ocular or respiratory administration, and in particular, tablets, simple or sugar-coated, sublingual tablets, sachets, packs, hard gelatin capsules, preparations to be dissolved under the tongue, bars, suppositories, creams, ointments, skin gels, injectable preparations or preparations to be swallowed, aerosols, eye .or nose drops, and the like.

The appropriate dosage varies according to the patient's age and weight, the administration route and the nature of the therapeutic indication and of any associated treatments, and ranges between 0.1 and 200 mg per day.

The examples which follow illustrate the invention but in no way limit the latter.

The preparations described below do not enable products of the invention to be obtained. They nevertheless enable intermediates to be obtained which are useful in the synthesis of the products of the invention.

PREPARATION 1:
TRICARBONYL{1-4-η-[(1E,3E)-1-ETHOXYCARBONYL-2-METHYL-5-OXO-1,3-PENTADIENYL]-}IRON

Stage A: Ethyl 4,4-Dimethoxy-3-Methyl-2-Butenoate

A mixture of 50 mmol of 1,1-dimethoxyacetone and 60 mmol of ethyl 2-(diethoxyphosphoryl)acetate is added in the course of 1 hour to a suspension of 125 mmol of potassium carbonate in 10 ml of water with vigorous stirring and with temperature maintained at between 20° and 30° C. When the addition is complete, stirring is continued for 24 hours at room temperature and the insoluble matter is then removed by filtration and washed with diethyl ether. The organic phase is separated and washed with saturated sodium chloride solution to neutrality. After drying and evaporation of the solvent, the product is purified by distillation under vacuum, which yields an (E+Z) isomer mixture in the form of an oil.

Stage B: Ethyl (E)-3-Methyl-4-Oxo-2-Butenoate 50 mmol of ethyl (E+Z)-4,4-dimethoxy-3-methyl-2-butenoate are placed in a buffered acetic medium (3 g of sodium acetate, 1.5 ml of water, 30 ml of acetic acid). The reaction medium is heated to 100° C. for 5 hours and the solvents are then removed under vacuum. After the residue is taken up with water and 100 ml of diethyl ether are added, the organic phase is separated and washed with 100 ml of saturated sodium chloride solution. After drying and evaporation of the solvents, purification is performed by distillation under vacuum, and yields the E stereoisomer.

Yield: 85%.
B.p.$_1$=44°–46° C.

Stage C: Ethyl (2E,4E)-3-Methyl-6-Oxo-2,4-Hexadienoates

A solution of 50 mmol of ethyl (E)-3-methyl-4-oxo-2-butenoate in 25 ml of benzene is added in the course of 10 minutes, with vigorous stirring and under a nitrogen atmosphere, to a benzene suspension (100 ml) of 50 mmol of formylmethylenetriphenylphosphorane, the temperature being maintained at about 0° C. After return to room temperature, the reaction medium is heated under reflux for 6 hours. After being cooled, the medium is poured into a water/ethyl ether mixture and the organic phase is then separated and dried. Evaporation of the solvents is followed by chromatography on a column of silica gel ($SiO_2$: 70–230 mesh; eluent: $CH_2Cl_2$), which yields an oil (mixture of isomers) from which the (E,E) isomer is separated by fractional crystallization.

Yield: 65%.

Stage D:
Tricarbonyl{1-4-η-[(1E,3E)-1-Ethoxycarbonyl-2-Methyl-5-Oxo-13-PENTADIENYL]}IRON A solution of 10 mmol of ethyl (2E,4E)-3-methyl-6-oxo-2,4-hexadienoate in 75 ml of toluene is outgassed with a stream of nitrogen for 30 minutes before the addition of 34 ml (21 mmol) of pentacarbonyliron, and is then irradiated. The photolysis is carried out in a pyrex cell cooled by water circulation with a Philips HPK 125 W lamp for 18 hours at a temperature in the region of 35° C. After evaporation of the solvent, the residue is purified by chromatography on a column of silica gel ($SiO_2$: 70–230 mesh; eluent: $CH_2Cl_2$), which yields a yellow oil (yield: 85%). Tricarbonyl{1-4-η-[(1E,3E)-1-alkoxycarbonyl-2-methyl-5-oxo-1,3-pentadienyl]}irons are obtained in the same manner using the appropriate alkyl 2-(diethoxyphosphoryl)acetate.

PREPARATION 2: ETHYL (E)-4-DIETHOXYPHOSPHORYL-3-METHYL-2-BUTENOATES

Stage A: Ethyl (E)-4-Hydroxy-3-Methyl-2-BUTENOATE 0.125 mmol of ethyl (E)-3-methyl-4-oxobutenoate, obtained in stage B, Preparation 1, dissolved in 100 ml of ethanol, is reduced with stirring and at a temperature below 20° C. with an aqueous-alcoholic solution of 4.72 g (125 mmol) of sodium borohydride. Stirring is continued for 1 hour after the addition is complete, the reaction medium is then filtered and the insoluble matter is washed with diethyl ether. After removal of the solvents, the residue is taken up with water and extracted with 3×100 ml of diethyl ether. After drying and evaporation of the solvents, the oil is purified by passage through a column of silica gel (eluent: dichloromethane; $SiO_2$: 70–230 mesh).

Yield: 76% Oil

Stage B: Ethyl (E)-4-Bromo-3-Methyl-2-Butenoates

Protected from moisture, with stirring and in the cold (0°–5° C.), 10.5 g (39 mmol) of phosphorus tribromide are added dropwise (10 minutes) to an ethereal solution (75 ml) of 100 mmol of ethyl (E)-4-hydroxy-3-methyl-2-butenoate, obtained above. After a contact time of 1 h 30 min, the reaction medium is poured into water. The organic phase is separated and washed with saturated sodium hydrogen carbonate solution to neutrality. After drying and evaporation of the solvent, the residue is chromatographed on a column of silica gel (eluent: dichloromethane; $SiO_2$: 70–230 mesh).

Yield: 91% Oil.

Stage C: Ethyl (E)-4-Diethoxyphosphoryl-3-Methyl-2-Butenoate 50 mmol of ethyl (E)-4-bromo-3-methyl-2-butenoate are heated to 130°–140° C. with protection from moisture. After the heating has been stopped, 50 mmol of triethyl phosphite are added dropwise so as to maintain the temperature at about 130° C.; the bromoethane formed becomes removed as soon as it appears. When the addition is complete, the reaction is completed by heating for 30 minutes to 150°–160° C. A distillation under vacuum enables the expected product to be collected.

Yield: 94%.

B.p.$_2$: 150°–152° C.

Alkyl (E)-4-diethoxyphosphoryl-3-methyl-2-butenoates are obtained in an identical manner using in stage A the alkyl (E)-3-methyl-4-oxobutenoate corresponding to the expected product.

EXAMPLE 1: ETHYL (E,E,E)-7-(6,8-DIMETHYL-2H-CHROMEN-3-YL)-3-METHYL-2,4,6-OCTATRIENOATE

Stage A: 6,8-Dimethyl-3-Acetyl-2H-Chromene 1.50 g (10 mmol) of 2-hydroxy-3,5-dimethylbenzaldehyde together with 0.66 g (10 mmol) of 3-oxo-1-butene are added at room temperature to a suspension of 0.14 g (1 mmol) of potassium carbonate in 50 ml of 2-butanone. The mixture is brought to reflux with stirring and this temperature is maintained for 90 minutes. The reaction medium is evaporated on a water bath under vacuum, and the residue is taken up with 100 ml of water and extracted 3 times with 75 ml of diethyl ether. The organic phases are combined, washed to neutrality with saturated aqueous sodium chloride solution, dried over sodium sulfate, filtered and evaporated on a water bath under vacuum, and chromatographed on a column of silica (70–230 mesh), eluting with dichloromethane.

Yield: 81%.

Stage B: 6,8-Dimethyl-3-(1-Hydroxyethyl)-2H-Chromene 2.02 g (10 mmol) of 6,8-dimethyl-3-acetyl-2H-chromene, obtained in the preceding stage, are dissolved in 50 ml of ethanol. A solution of 0.38 g (10 mmol) of sodium borohydride in 5 ml of aqueous sodium hydroxide solution is added in a single portion with magnetic stirring. Stirring is maintained for 2 hours and the solvent mixture is then evaporated off. The residue is taken up with 50 ml of water and extracted 3 times with 50 ml of diethyl ether. The ethereal solution is washed with saturated aqueous sodium chloride solution until the washing liquors are neutral, and the organic phase is dried and evaporated.

Yield: 86%.

Stage C: [1-(6,8-Dimethyl-2H-Chromen-3-yl)-Ethyl]Triphenylphosphonium Bromide 2.04 g (10 mmol) of 6,8-dimethyl-3-(1-hydroxyethyl)-2H-chromene, obtained in the preceding stage, and 3.43 g (10 mmol) of triphenylphosphonium bromide in 80 ml of methanol are placed under a nitrogen atmosphere at room temperature. The mixture is stirred for 96 hours. The residue obtained is removed on a column of silica gel (70–230 mesh), using a methylene chloride/ethanol (95/5 v/v) mixture as elution solvent, and the product is crystallized in benzene.

Yield: 68%.

Melting point: 164° C.

Stage D: Ethyl (E,E,E)-7-(6,8-Dimethyl-2H-Chromen-3-yl)-3-Methyl-2,4,6-Octatrienoate 70 ml of a solution of n-butyllithium in hexane (1.6M) are added in the course of 10 minutes, with stirring, at room temperature and under an inert atmosphere, to a suspension of 5.29 g (10 mmol) of [1-(6,8-dimethyl-2H-chromen-3-yl)ethyl]triphenylphosphonium bromide in 50 ml of tetrahydrofuran. Stirring is continued for 15 minutes and the mixture is cooled to a temperature of between −15° C. and −20° C. 3.06 g (10 mmol) of tricarbonyl{1-4-η-[(1E,3E)-1-ethoxycarbonyl-2-methyl-5-oxo-1,3-pentadienyl]}iron, obtained in Preparation 1, are added in a single portion. The reaction medium is maintained at room temperature with stirring for 18 hours. It is poured into 75 ml of water and extracted three times with 100 ml of diethyl ether. The organic phases are combined and washed to neutrality with saturated aqueous sodium chloride solution. The organic phase is dried over sodium sulfate and filtered, and the diethyl ether is evaporated off. The product is purified by a chromatographic run on silica gel.

The product obtained is then brought into contact with 11.15 g of trimethylamine N-oxide dihydrate in 50 ml of methylene chloride. The mixture is heated under reflux for 5 hours. It is cooled, poured into 100 ml of water and extracted three times with 75 ml of dichloromethane. The organic phases are combined and dried over sodium sulfate, and the solvent is evaporated off. The residue is purified by chromatography on silica gel (70–230 mesh), and the product obtained is recrystallized in diisopropyl ether.

Yield: 20%.

Melting point: 122° C.

Elemental analysis: Calculated: C: 78.07 H: 7.74. Found: C: 77.41 H: 8.14.

Spectral characteristics: Infrared Absorption at 1700, 1610, 1160 and 960 $cm^{-1}$.

Nuclear magnetic resonance (60 MHz)

Solvent $CDCl_3$.

$\delta = 1.30$ ppm; triplet 3H $CH_3$ ester J=7Hz.

$\delta = 2.00$ to 2.45 ppm; 4 singlets 4×3H 4$CH_3$ (chromene+chain).

$\delta = 4.25$ ppm; quartet 2H $CH_2$ ester J=7Hz.

$\delta = 4.85$ ppm; 2H $CH_2$ chromene.

$\delta = 5.75$ to 7.45 ppm; 7H; multiplet; aromatic and ethylenic.

EXAMPLE 2: ETHYL 7-(2H-CHROMEN-3-YL)-3-METHYL-2,4,6-OCTATRIENOATE

Stage A: 3-Acetyl-2H-Chromene 1.22 g (10 mmol) of salicylaldehyde together with 0.66 g (10 mmol) of 3-oxo-1-butene are added at room temperature to a suspension of 0.14 g (1 mmol) of potassium carbonate in 50 ml of 2-butanone. The mixture is brought to reflux with stirring and this temperature is maintained for 4 hours. The procedure is then as in Example 1, stage A. The final chromatography is replaced by a recrystallization in hexane.

Yield: 57%.

Melting point: 58°–60° C.

Stage B: 3-(1-Hydroxyethyl)-2H-Chromene

The procedure is as in Example 1, stage B, 6,8-dimethyl-3-acetyl-2H-chromene being replaced by 3-acetyl-2H-chromene, obtained in the preceding stage.

Yield: 95%.

Stage C: [1-(2H-Chromen-3-yl)Ethyl]Triphenylphosphonium Bromide

The procedure is as in Example 1, stage C, 6,8-dimethyl-3-(1-hydroxyethyl)-2H-chromene being replaced by 3-(1-hydroxyethyl)-2H-chromene.

Yield: 98%.

Stage D: Ethyl 7-(2H-Chromen-3-yl)-3-Methyl-2,4,6-Octatrienoate

The procedure is as in Example 1, stage D.

Crystallization solvent: dichloromethane.

Yield: 30%.

EXAMPLE 3: ETHYL (E,E,E)-7-(6-CHLORO-8-METHYL-2H-CHROMEN-3-YL)-3-METHYL-2,4,6-OCTATRIENOATE

Stage A: 6-Chloro-8-Methyl-3-Acetyl-2H-Chromene

Using the procedure described in Example 1, stage A, but with 2-hydroxy-3,5-dimethylbenzaldehyde replaced by 2-hydroxy-3-methyl-5-chlorobenzaldehyde, the expected product is obtained, and this is purified by an additional recrystallization in an isopropyl ether/petroleum ether mixture.

Melting Point: 78°–79° C.

Stage B: Ethyl 3-(6-Chloro-8-Methyl-2H-Chromen-3-yl)-2-Butenoate

A volume of dimethoxymethane sufficient to cover 0.108 g-at. of zinc is added into a round-bottomed flask equipped with a stirrer, a dropping funnel, a condenser and a thermometer. A few drops of pure ethyl bromoacetate are then added. The reaction is primed by gentle heating (with the flame of a lighter). The reaction is then maintained by the dropwise addition of 0.1 mmol of ethyl bromoacetate dissolved in anhydrous dimethoxymethane. The rate of addition is adjusted so that the temperature does not exceed 40° C. After the addition, the reaction medium is stirred for a further 30 minutes at room temperature, and 0.083 mmol of 3-acetylchromene, dissolved in anhydrous THF, is then added in a single portion. The reaction medium is stirred for a further 15 minutes and then hydrolyzed with saturated ammonium chloride solution. After 3 successive extractions with ethyl acetate, the organic extracts are dried over magnesium sulfate and the solvents removed. 50 mmol of the expected product are dissolved in 50 ml of benzene and 1 ml of phosphorus oxychloride is added. The mixture is brought to reflux for 1 h 30 min. After being cooled, the reaction medium is poured into 100 ml of water. The benzene phase is decanted and the aqueous phase extracted with 2×50 ml of diethyl ether. After the organic extracts have been washed with saturated sodium hydrogen carbonate solution to neutrality and dried and the solvents have been removed, the ester is purified on a column of silica gel (SiO$_2$: 70–230 mesh; eluent CH$_2$Cl$_2$).

Spectral characteristics: $^1$H NMR δ: ppm (s: singlet; t: triplet; q: quartet; b.s.: broad signal) 1.30 (3H, t, J=7 Hz, OCH$_2$CH$_3$); 2.15 (3H, s, CH$_3$ at 8-position); 2.45 (3H, b.s., C$\underline{H}_3$) 4.20 (2H, q, J=7Hz, OC$\underline{H}_2$CH$_3$); 4.95 (3H, s); 5.65 (1H, b.s.,

6.75, 6.90, 6.95 (3H, b.s., H$_4$, H$_5$ and H$_7$)

Stage C: 3-(6-Chloro-8-Methyl-2H-Chromen-3-yl)-2-Butenol

Protected from moisture, with stirring and in the cold (−15°, −10° C.), a solution of 20 mmol of the ester obtained in stage B in 70 ml of diethyl ether (or tetrahydrofuran) is added dropwise to 20 mmol of lithium aluminum hydride suspended in the same solvent. When the temperature has returned to room temperature, stirring is continued for 2 hours, and the excess hydride is then destroyed by the cautious addition of ethyl and then water. The medium is then acidified (pH 2–3). After drying and evaporation of the solvents, the crude product is directly subjected to oxidation.

Yield: 95%.

Spectral characteristics: Infrared: 3400 νOH. 1610 νC=C. 1235 νC=O.

Stage D: (E)-3-(6-Chloro-8-Methyl-2H-Chromen-3-yl)-2-Butenal

A solution of 20 mmol of the chosen alcohol in 50 ml of dichloromethane is added slowly in the cold (−15°, −10° C.) and with stirring to 400 mmol of manganese dioxide suspended in the minimum amount of dichloromethane. When the addition is complete, stirring is continued with cooling for 1 to 3 hours, and the medium is then filtered. After evaporation of the solvent, the product obtained is purified on a column of silica gel (SiO$_2$: 70–230 mesh), eluting with dichloromethane.

Yield: 20%.

Stage E: Ethyl (E,E,E)-7)-(6-Chloro-8-Methyl-2-H-Chromen-3-yl)-2,4,6-Ocatrienoate 3 ml of a hexane solution of n-butyllithium (1.6M) are added under a nitrogen atmosphere and at room temperature to 1.20 g (4.54 mmol) of ethyl (E)-4-diethoxyphosphoryl-3-methyl-2-butenoate, obtained in Preparation 2, dissolved in 10 ml of anhydrous THF. When the addition is complete, stirring is continued for 15 minutes (reddish coloration of the reaction medium), and 0.91 g (4.54 mmol) of chromene aldehyde obtained in the preceding stage, dissolved in 5 ml of THF, is then added; stirring is maintained for 3 hours at room temperature. The reaction medium is then poured into 100 ml of water and extracted with 3×25 ml of diethyl ether. After drying and evaporation of the solvents, the residue is chromatographed on a column of silica gel (2 chromatographic runs on SiO$_2$ 70–230 mesh, eluent CH$_2$Cl$_2$, and a third on SiO$_2$ 230–400 mesh, eluent CH$_2$Cl$_2$). 400 mg of a yellow solid are then obtained, and this is recrystallized in methylene chloride.

Melting point: 107° C.

EXAMPLE 4: ETHYL 7-(2H-CHROMEN-3-YL)-3-METHYL-2,4,6-OCTATRIENOATE

Using the procedure discovered in Example 3, but with 2-hydroxy-3-methyl-5-chlorobenzaldehyde replaced by salicylaldehyde, the product of the title of Example 2 is obtained.

In stage 3, the contact time will, however, be changed to 48 hours.

Melting point: 107° C.

EXAMPLES 5 TO 9

By replacing in Example 1, stage A * 2-hydroxy-3,5-dimethylbenzaldehyde by:

2-hydroxy-5-chloro-3-methylbenzaldehyde, ethyl (E,E,E)-7-(6-chloro-8-methyl-2H-chromen-3-yl)-3-methyl-2,4,6-ocatrienoate is obtained (EXAMPLE 5)

2-hydroxy-5,6-dimethyl-4-methoxybenzaldehyde, ethyl (E,E,E)-7-(5,6-dimethyl-7-methoxy-2H-chromen-3-yl)-3-methyl-2,4,6-octatrienoate is obtained (EXAMPLE 6)

2-hydroxy-4-methoxybenzaldehyde, ethyl (E,E,E)-7-(7-methoxy-2H-chromen-3-yl)-3-methyl-2,4,6-octatrienoate is obtained (EXAMPLE 7)

2-hydroxy-5-methoxybenzaldehyde, ethyl (E,E,E)-7-(6-methoxy-2H-chromen-3-yl)-3-methyl-2,4,6-octatrienoate is obtained (EXAMPLE 8)

2-hydroxy-3,5-dichlorobenzaldehyde, ethyl (E,E,E)-7-(6,8-dichloro-2H-chromen-3-yl)-3-methyl-2,4,6-octatrienoate is obtained (EXAMPLE 9)

The compounds of the Examples 5 to 9 may also be obtained using the procedure described for Example 3.

PHARMACOLOGICAL STUDY:

EXAMPLE 10: INHIBITION OF GROWTH OF L1210 LINE

The growth of this mouse leukemic line is assessed by the capacity of the cells to incorporate tritiated thymidine. The degree of incorporation is measured 48 hours after the introduction of the test compounds into the culture medium.

The compound No. 1 possesses, in this test, a growth inhibition dose (IC$_{50}$) of 25 μM, whereas that of etretinate is 80 μM.

EXAMPLE 11: STUDY OF THE TOXICITY ON THE HUMERI OF RAT FETUSES OF GESTATIONAL AGE 21 DAYS

The toxicity of retinoids can be evaluated on humeri of rat fetuses explanted in vitro as described by KISTLER (1985).

Retinoid activity results in a release of proteoglycans from the bone matrix. This release is assessed after 7 days of culture in vitro by assaying the concentration of proteoglycans in the medium, by the method of WITHEMAN (1973).

The compounds of the present invention prove completely incapable of stimulating the release of proteoglycans from the bone matrix of the humeri of rat fetuses at a concentration of 100 μM, whereas etretinate permits a significant release of these proteoglycans at a dose of 40 μM.

EXAMPLE 12: DETECTION OF AN EXCESS-VITAMIN A TYPE TOXICITY IN VIVO

The side effects limiting the use of retinoid agents in human clinical medicine are reflected in the appearance of a hypervitaminosis A syndrome; this can be reproduced experimentally in animals.

The selected treatment protocol is a daily injection for five days, repeated a second time after an interval of two days. It is identical to that used by BOLLAG et al (1981).

Whereas retinoic acid and etretinate cause a rapid weight loss, the appearance of alopecia and bone weakening, manifestations of their toxicity, compounds of the present invention proved devoid of excess-vitamin A type toxicity: no statistically significant sign in respect of weight, no fracture detectable by radiography and no onset of alopecia were reported following treatment with the compounds of the invention.

We claim:

1. A compound selected from those of formula:

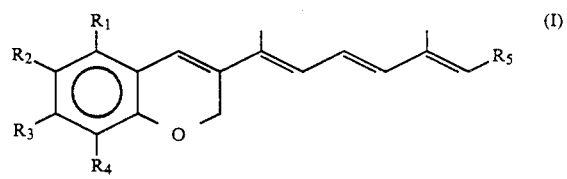

in which:
R$_1$, R$_2$, R$_3$ and R$_4$, which may be identical or different, denote a hydrogen atom, a halogen atom or a lower alkyl, lower alkenyl, lower alkyloxy or lower alkenyloxy group, optionally substituted with one or more halogen atoms, R$_5$ denotes a carboxyl, (lower alkyloxy)carbonyl, (lower alkenyloxy)carbonyl or (lower alkynyloxy)carbonyl, a stereoisomer thereof and an addition salt thereof with a pharmaceutically-acceptable base when R$_5$ denotes a carboxyl group.

2. A compound as claimed in claim 1, in which the configuration is (E,E,E).

3. A compound as claimed in claim 1, which is ethyl (E,E,E)-7-(6,8-dimethyl-2H-chromen-3-yl)-3-methyl-2,4,6-octatrienoate.

4. A compound as claimed in claim 1, which is ethyl (E,E,E,)-7-(2H-chromen-3-yl)-3-methyl-2,4,6-octatrienoate.

5. A compound as claimed in claim 1, which is ethyl (E,E,E)-7-(6-chloro-8-methyl-(2H-chromen-3-yl)-3-methyl-2,4,6-octatrienoate.

6. A compound as claimed in claim 1, which is ethyl 7-(2H-chromen-3-yl)-3-methyl-2,4,6-octatrienoate.

7. A pharmaceutical composition, useful in inhibiting the growth of a tumor or neoplasm of the L1210 cell line type or treating a skin disorder of the epithelial type, which is susceptible to treatment with retinoid-type chemotherapeutic agents, containing, as active principle, an effective amount of at least one compound as claimed in claim 1 in combination with one or more pharmaceutically-acceptable, non-toxic, inert vehicles or excipients.

8. Method for inhibiting the growth of a tumor or neoplasm of the L1210 cell line type or treating a skin disorder of the epithelial type, which is susceptible to treatment with retinoid-type chemotherapeutic agents, comprising the step of administering to a subject afflicted with such ailment an amount of at least one compound as claimed in claim 1 which is effective for such purpose.

* * * * *

UNITED STATES PATENT AND TRADEMARK OFFICE
CERTIFICATE OF CORRECTION

PATENT NO. : 4,975,454

DATED : Dec. 4, 1990

INVENTOR(S) : Jean-Daniel Brion, Guillaume Le Baut, Patrick Ducrey, Sylvie Piessard-Robert, Claude Cudennec, Geneviève Seurre It is certified that error appears in the above-identified patent and that said Letters Patent is hereby corrected as shown below:

Column 6, line 31; "-13-" should read -- -1,3- --.
Column 10, approximately line 34; "ethyl and" should read
    -- ethyl acetate and --.
Column 10, line 55; "-2-H-" should read -- -2H- --.
Column 11, line 25; move the comma at the beginning of the line
    to the end of line 24 after "E", second occurrence, and cancel
    the dash at the end of line 24.
Column 12, line 24; "of formula:" should read -- of the
    formula: --. (R&A 1-30-90, p. 1)
Column 12, approximately line 53; "(E,E,E,)" should read
    -- (E,E,E) --.
Column 12, line 56; "-(2H-" should read -- -2H- --.

Signed and Sealed this

Fourth Day of June, 1991

Attest:

HARRY F. MANBECK, JR.

Attesting Officer  Commissioner of Patents and Trademarks